(12) United States Patent
Inana

(10) Patent No.: US 9,075,048 B2
(45) Date of Patent: Jul. 7, 2015

(54) ASSAY APPARATUS AND ITS CONTROL METHOD AND REACTION CONTAINER FOR ASSAY

(71) Applicant: FUJIFILM Corporation, Tokyo (JP)

(72) Inventor: Katsuya Inana, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 13/851,869

(22) Filed: Mar. 27, 2013

(65) Prior Publication Data

US 2013/0217150 A1 Aug. 22, 2013

Related U.S. Application Data

(63) Continuation of application No. PCT/JP2011/005416, filed on Sep. 27, 2011.

(30) Foreign Application Priority Data

Sep. 28, 2010 (JP) ................. 2010-216923

(51) Int. Cl.
*G01N 35/00* (2006.01)
*G01N 33/53* (2006.01)

(52) U.S. Cl.
CPC .......... *G01N 33/5304* (2013.01); *B01L 2200/14* (2013.01); *B01L 2200/141* (2013.01); *G01N 35/00613* (2013.01); *G01N 35/00732* (2013.01); *G01N 35/00663* (2013.01)

(58) Field of Classification Search
None
See application file for complete search history.

(56) References Cited

U.S. PATENT DOCUMENTS

| 4,981,786 | A | 1/1991 | Dafforn et al. |
| 2003/0049848 | A1 | 3/2003 | Gebrian et al. |
| 2007/0077645 | A1 | 4/2007 | Aoyagi |
| 2007/0110638 | A1* | 5/2007 | Heiner et al. ............ 422/130 |
| 2008/0153153 | A1 | 6/2008 | Takenaka et al. |
| 2008/0166821 | A1 | 7/2008 | Oyamada et al. |
| 2009/0053689 | A1* | 2/2009 | Oviso et al. ............ 435/5 |

FOREIGN PATENT DOCUMENTS

| EP | 0 306 336 A2 | 3/1989 |
| EP | 0 306 336 A3 | 3/1989 |
| JP | 6-265557 A | 9/1994 |
| JP | 2007-101364 A | 4/2007 |

(Continued)

OTHER PUBLICATIONS

Chinese Office Action dated Sep. 4, 2013, with English translation.

(Continued)

*Primary Examiner* — Melanie Y Brown
*Assistant Examiner* — Rebecca Martinez
(74) *Attorney, Agent, or Firm* — McGinn IP Law Group, PLLC

(57) ABSTRACT

In an assay apparatus for performing an assay related to a specimen received from the outside thereof based on a reaction between the specimen and a reagent by using a reaction container that holds the reagent, the apparatus includes a detection means that detects a state in which an assay has ended before completion, and a mark providing means that provides a predetermined mark for the reaction container when the state in which the assay has ended before completion is detected by the detection means.

10 Claims, 6 Drawing Sheets

(56) References Cited

FOREIGN PATENT DOCUMENTS

| JP | 2008-139297 A | 6/2008 |
| JP | 2008-157829 A | 7/2008 |
| JP | 2009-133813 A | 6/2009 |
| JP | 2009-287952 A | 12/2009 |
| JP | 2010-071828 A | 4/2010 |
| JP | 2010-156571 A | 7/2010 |
| WO | WO 02/071069 A1 | 9/2002 |
| WO | WO 03/022441 A1 | 3/2003 |
| WO | WO 2009/125676 A1 | 10/2009 |

OTHER PUBLICATIONS

Chinese Office Action dated Jan. 24, 2014, with English translation.
Chinese Office Action dated May 4, 2014 with English Translation thereof.
International Search Report in PCT/JP2011/005416 dated Nov. 8, 2011 (English Translation Thereof).
Extended Search Report dated Mar. 11, 2014.
European Office Action dated Jan. 7, 2015.

\* cited by examiner

ASSAY APPARATUS AND ITS CONTROL METHOD AND REACTION CONTAINER FOR ASSAY

BACKGROUND OF THE INVENTION

1. Field of the Invention

The present invention relates to an assay apparatus, and particularly to an assay apparatus for performing a predetermined assay using a reaction container that holds a specimen, and a method for controlling the assay apparatus.

Further, the present invention relates to a reaction container that holds a specimen, and which is used in such an assay apparatus.

2. Description of the Related Art

In recent years, many devices for assay that can easily and quickly test an analyte by using an assay method, such as immunoassay, were developed. In such devices for assay, a specimen (sample) that may contain an analyte is held by a carrier, and assayed. Further, various devices for testing in-vitro diagnostic reagents, toxic substances or the like are commercially available. Some example of such devices uses immunochromatography, as disclosed in Japanese Unexamined Patent Publication No. 2008-139297 (Patent Document 1). When a device adopting immunochromatography is used, an assay result is obtainable by leaving a specimen solution held by a carrier for only about 5 to 10 minutes at the shortest. Therefore, assay techniques using assay methods, such as immunoassay, are widely adopted as simple and quick assay techniques, for example, in a clinical test at a hospital, an assay test at a laboratory, or the like.

Especially, in medical care situations at a doctor's office, a clinic, home and the like, many immunochromatographic assay apparatuses (immunochromato-readers) are used as assay devices for POCT (Point of Care Testing) care. In POCT, a simple assay is possible without relying on a clinical test specialist. The immunochromatographic assay apparatus can measure the color-developed state of a reagent in a device loaded into the apparatus at high sensitivity. Therefore, even if the color-developed state is too low to visually judge the state, a highly sensitive and reliable assay is possible. Japanese Unexamined Patent Publication No. 2009-133813 (Patent Document 2) discloses an example of this kind of assay apparatus.

In the aforementioned assay methods, it is necessary to detect an extremely small amount of analyte at high sensitivity. As an assay method satisfying such a need, a method that performs amplification (sensitization), for example, as disclosed in Japanese Unexamined Patent Publication No. 2009-287952 (Patent Document 3) is known. In this method, after an analyte is developed on a carrier, washing liquid is supplied to wash away everything except a labeling substance captured by binding to a specific reaction site on the carrier. After then, a sensitizing solution is supplied onto the carrier to sensitize the labeling substance. Accordingly, a very small amount of analyte becomes detectable at high sensitivity.

Here, the aforementioned sensitizing process may be performed only if necessary. In other words, if the color-developed state of a reagent has been measured by ordinary processing, measurement may end. If the color-developed state is not measurable by ordinary processing, the sensitizing process may be performed, and the color-developed state may be measured after the sensitizing process.

The aforementioned carrier is used by being held in a reaction container that is called as a cartridge, a package, an assay kit, or the like in general. Japanese Unexamined Patent Publication No. 2007-101364 (Patent Document 4) discloses an example of such a kind of reaction container. As disclosed also in Patent Document 4, a protective sheet is often provided for the reaction container to prevent leakage or quality change of a reagent or the like that is held in advance in the reaction container. The protective sheet is broken by the assay apparatus to make use of the reagent or the like during use of the reaction container. Therefore, it is possible to judge whether the reaction container has already been used or the reaction container has not been used by checking whether this protective sheet is broken.

SUMMARY OF THE INVENTION

However, when a reaction container or the like is structured in such a manner that the aforementioned sensitizing process is possible, if judgment as to whether the reaction container or the like has been used or not is based on the state of the protective sheet, the judgment is wrong in some cases. This point will be described by using an example in which a protective sheet for protecting a sensitizing solution is provided in a reaction container. When the reaction container is used, if the color-developed state of a reagent has been able to be measured by ordinary processing, measurement ends at that time, and the reaction container is removed from the assay apparatus. Since no sensitizing process has been performed, the protective sheet for protecting the sensitizing solution is not broken. However, in this case, a reagent used in ordinary processing has been used. Therefore, if it is judged that the reaction container has not been used based on the state of the protective sheet that is not broken, and the reaction container is used again in an assay, naturally only a wrong assay result is obtainable.

Further, not only when a reaction container is structured in such a manner that the sensitizing process is possible, but also when another type of reaction container is used, after an assay is started by setting a reaction container in an assay apparatus, the assay may be aborted for some reasons. In such a case, the reaction container is not usable again, but the protective sheet for protecting a reagent is not broken in some cases. Also in such a case, if it is judged that the reaction container has not been used based on the state of the protective sheet that is not broken, and the reaction container is used again in an assay, naturally only a wrong assay result is obtainable.

In view of the foregoing circumstances, it is an object of the present invention to provide an assay apparatus that can prevent reuse of a used reaction container, and a method for controlling the assay apparatus.

Further, it is another object of the present invention to provide a reaction container for assay that can prevent its reuse when it has been used.

An assay apparatus of the present invention is an assay apparatus for performing an assay related to a specimen received from the outside thereof based on a reaction between the specimen and a reagent by using a reaction container that holds the reagent, the apparatus comprising:

a detection means that detects a state in which an assay has ended before completion; and a mark providing means that provides a predetermined mark for the reaction container when the state in which the assay has ended before completion is detected by the detection means.

Here, the expression "an assay has ended before completion" means that not all the assay that is performable by using the reaction container set in the assay apparatus is completed. Specifically, for example, when the aforementioned sensitizing process is performable in a reaction container, it is defined that all the assay is completed when the process till measurement of a color developed state after the sensitizing process has been performed. Therefore, even if a valid assay result is obtained only by ordinary processing without sensitizing process, that is defined as a case in which "an assay has ended before completion". Further, when an assay process is aborted for some reasons after the reaction container is set in the assay apparatus, that is naturally defined as a case in which "an assay has ended before completion".

As the mark providing means, a means that makes a hole, as the mark, in the surface of the reaction container is desirably used. In such a case, it is desirable that a means that is used to break a protective sheet protecting the reagent is used also as the mark providing means.

The mark providing means is not limited to the aforementioned means. A means that draws a mark on the surface of the reaction container with oil-based ink or the like may be adopted as the mark providing means.

Meanwhile, a first reaction container for assay according to the present invention is applied to an assay apparatus using, as the mark providing means, a means that makes a hole, as the mark, in the surface of the reaction container. Further, an opening is provided on a surface of the reaction container, and the opening is covered by a sheet material that is breakable by the mark providing means.

It is desirable that the first reaction container for assay according to the present invention adopts a double sheet structure formed by providing, under the breakable sheet material, another sheet material for sealing the reagent with a space from the breakable sheet material.

Further, a second reaction container for assay according to the present invention is also applied to an assay apparatus using, as the mark providing means, a means that makes a hole, as the mark, in the surface of the reaction container. Further, a part of the surface of the reaction container has a low strength so that the hole is made by the mark providing means.

Further, a method for controlling an assay apparatus according to the present invention is characterized in that when a reaction container for assay adopting the double sheet structure is used in an assay apparatus using, as the mark providing means, a hole making means that makes a hole in the surface of the reaction container, when the assay is performed, both of the breakable sheet material and the other sheet material are broken to allow the reagent to flow out, and when the hole, as the mark, is made, only the breakable sheet material is broken.

According to the assay apparatus of the present invention, a detection means that detects a state in which an assay has ended before completion and a mark providing means that provides a predetermined mark for the reaction container when the state in which the assay has ended before completion is detected by the detection means are provided. Therefore, users of the assay apparatus can clearly recognize whether the reaction container has been used once in an assay, or the reaction container has not been used, for example, by checking whether the mark is provided in the reaction container in the vicinity of the assay apparatus. Hence, it is possible to certainly prevent obtainment of a wrong assay result by erroneously using a used reaction container again.

Further, in a first reaction container for assay according to the present invention, an opening is provided on a surface of the reaction container, and the opening is covered by a sheet material that is breakable by the mark providing means. Therefore, when the reaction container has not been used, the opening is not seen, but after the reaction container is used once in an assay, the sheet material is broken, and a hole made in the sheet material is seen. Therefore, it is possible to judge whether the reaction container has been used or not by checking whether this hole is present or not. Hence, it is possible to prevent erroneous reuse of a used reaction container.

Further, in a second reaction container for assay according to the present invention, a part of the surface of the reaction container has a low strength so that the hole is made by the mark providing means. Therefore, when the reaction container has not been used, the hole is not seen, but after the reaction container is used once in an assay, a hole made on the surface of the reaction container is seen. Therefore, also in this case, it is possible to judge whether the reaction container has been used or not by checking whether the hole is present or not. Hence, it is possible to prevent erroneous reuse of a used reaction container.

Further, according to a method for controlling an assay apparatus of the present invention, when a reaction container for assay adopting the double sheet structure is used in an assay apparatus using, as the mark providing means, a hole making means that makes a hole in the surface of the reaction container, when the assay is performed, both of the breakable sheet material and the other sheet material are broken, and when the hole, as the mark, is made, only the breakable sheet material is broken. Therefore, it is possible to prevent unnecessary flow of reagent when a hole, as a mark, is made.

DESCRIPTION OF THE PREFERRED EMBODIMENTS

Figure 1:
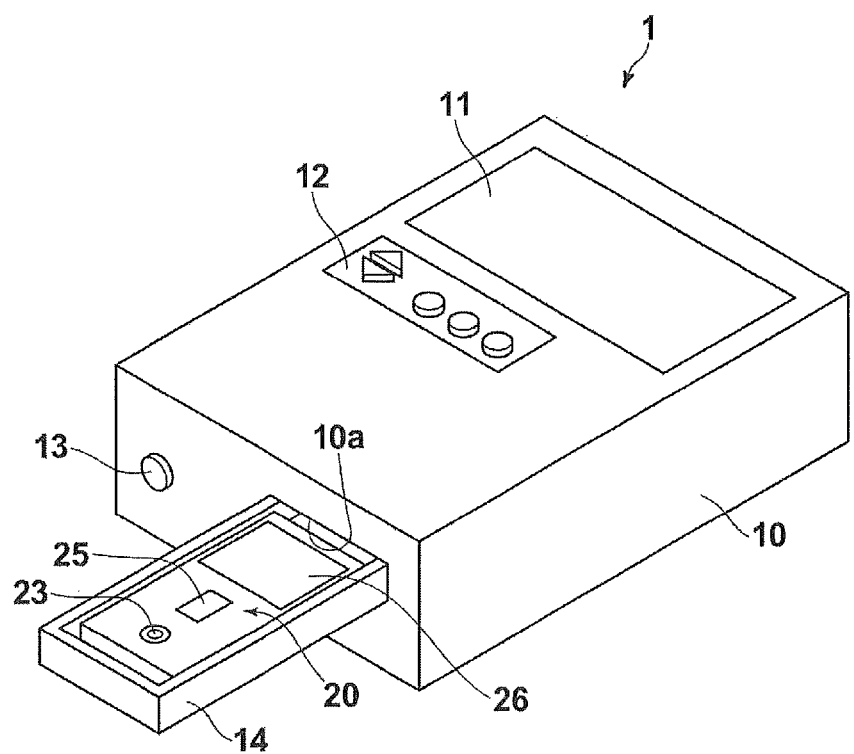
FIG. 1 is a perspective view illustrating an assay apparatus according to an embodiment of the present invention.
Figure 2:
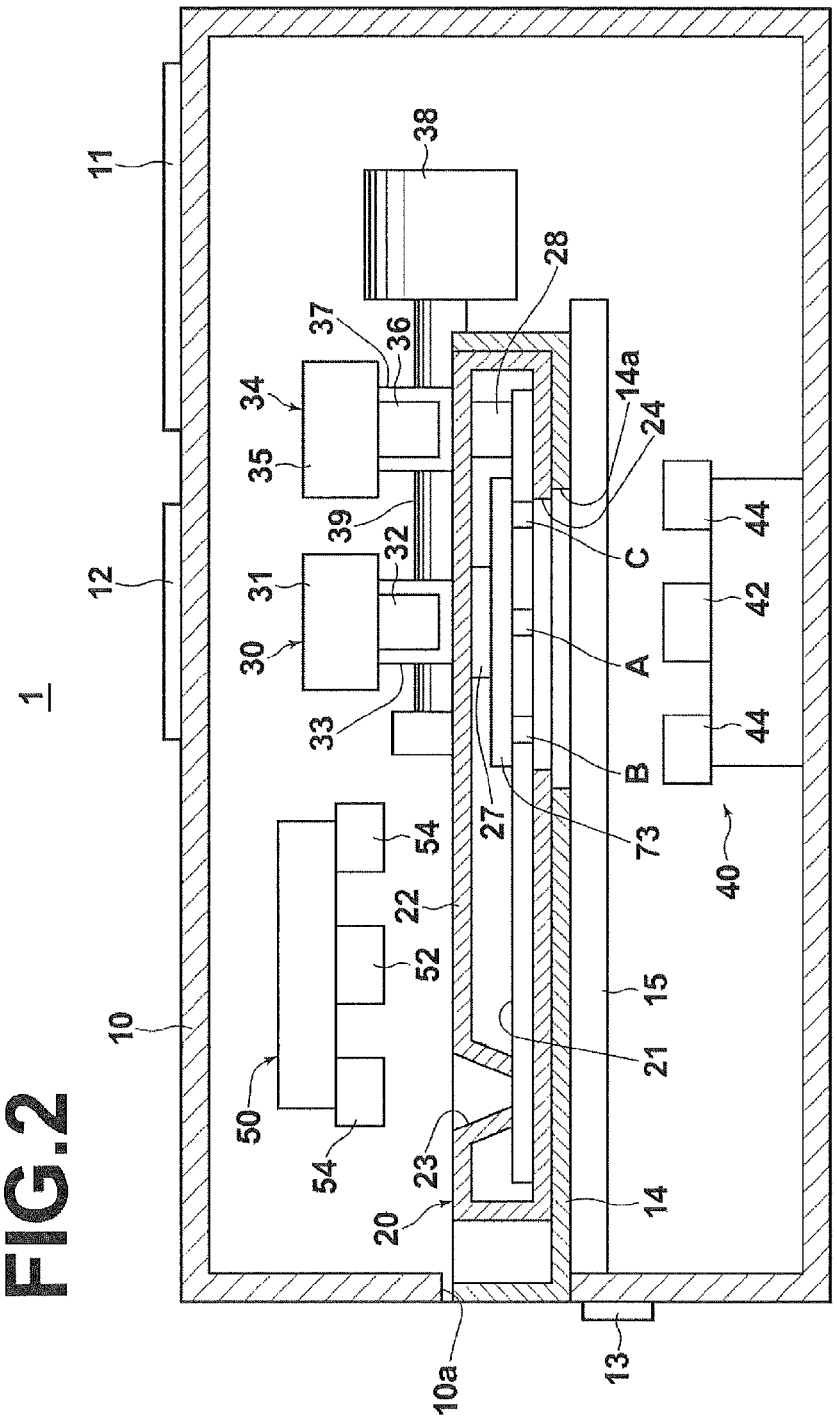
FIG. 2 is a partially-broken side view of the assay apparatus.
Figure 3:
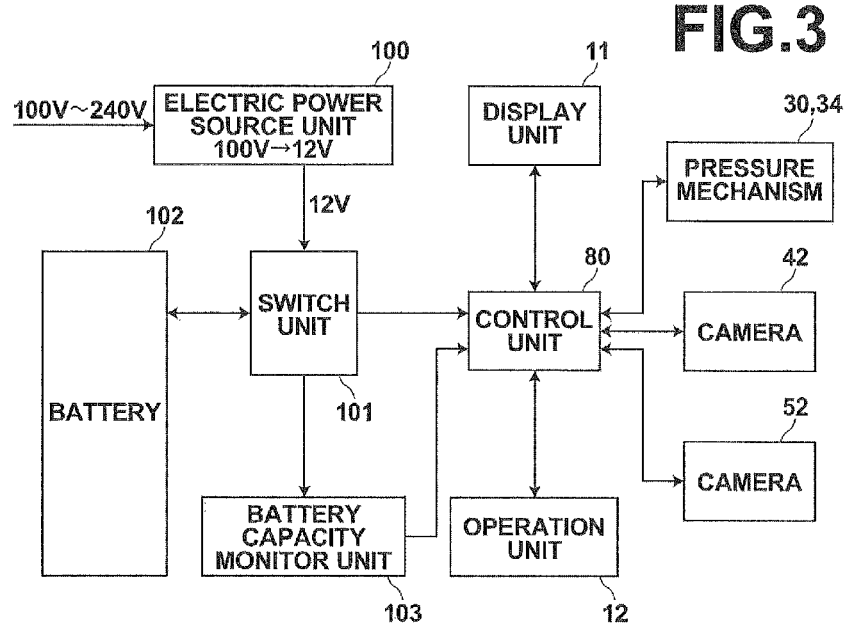
FIG. 3 is a block diagram illustrating the electrical configuration of the assay apparatus.

Hereinafter, embodiments of the present invention will be described in detail with reference to drawings. FIG. 1 is a perspective view of a chromatographic assay apparatus 1 according to an embodiment of the present invention. FIG. 2 is a partially-broken side view of the chromatographic assay apparatus 1. FIG. 3 is a diagram illustrating the electrical configuration of the chromatographic assay apparatus 1. First, the basic structure of the chromatographic assay apparatus 1 of the present invention will be described with reference to FIGS. 1 and 2.

As illustrated in these diagrams, the chromatographic assay apparatus 1 includes a case 10 having an opening 10a on the front side thereof, a display unit 11 arranged on the upper surface of the case 10, an operation unit 12 for operating a menu displayed on the display unit 11, an electric power switch 13, and a cartridge loading unit 14 for loading a cartridge for chromatography (a reaction container for assay) 20 into the apparatus. Further, the chromatographic assay apparatus 1 has a rail 15 that guides the cartridge loading unit 14 in such a manner that the cartridge loading unit 14 is movable in the horizontal direction in FIG. 2, pressure units 30, 34 for squeezing a washing liquid pot 27 and a sensitizing solution pot 28, which will be described later, respectively, and a first measurement unit 40 and a second measurement unit 50 for obtaining information from the cartridge 20 in the case 10.

The cartridge loading unit 14 is automatically or manually movable along the rail 15. When a most part of the cartridge loading unit 14 has moved to the outside of the case 10 through the opening 10a, a cartridge 20, into which assay solution (specimen) was supplied as will be described later, is loaded on the cartridge loading unit 14. After then, the cartridge loading unit 14 is pushed into the case 10, as illustrated in FIG. 2. Accordingly, the cartridge 20 is loaded into the chromatographic assay apparatus 1.

Figure 4:
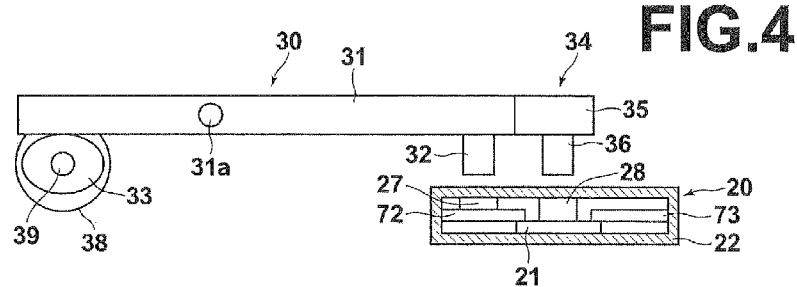
FIG. 4 is a front view illustrating a part of the assay apparatus.

FIG. 4 is a front view of the pressure units 30, 34, viewed from the left side of FIG. 2. Here, a broken view of the cartridge 20 is illustrated. With reference to FIG. 4, the pressure units 30, 34 will be described. The pressure unit 30 includes an arm 31 that is pivotable like a seesaw around a shaft 31a, a pressure portion 32 fixed onto a lower surface of a leading end of the arm 31, and a cam 33 arranged on the lower side of a rear end of the arm 31. The cam 33 is connected to a drive shaft 39 that is rotated by a motor 38, for example, in such a manner that the cam 33 is disconnectable from the drive shaft 39 through an electromagnetic clutch or the like, which is not illustrated. When the cam 33 rotates, the rear end of the arm 31 is moved up, and the pressure portion 32 at the leading end is moved down. Further, the other pressure unit 34 includes an arm 35, a pressure portion 36, and a cam 37, and is structured in a similar manner to the pressure unit 30.

Here, the pressure portion 32 of the pressure unit 30 and the pressure portion 36 of the pressure unit 34 are arranged in such a manner that the pressure portion 32 and the pressure portion 34 are located just above the washing liquid pot 27 and the sensitizing solution pot 28 arranged in the cartridge, respectively, when the cartridge 20 is placed at a predetermined position in the case 10.

Figure 5:
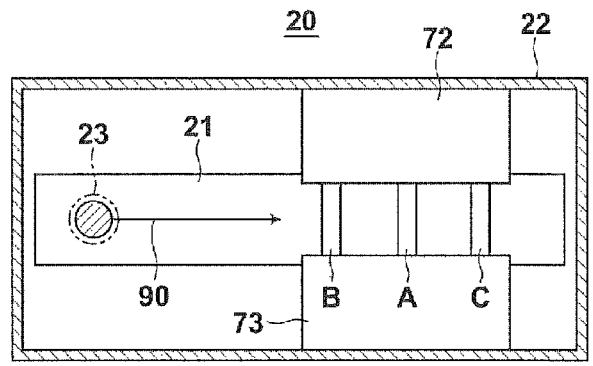
FIG. 5 is a partially-broken plan view illustrating a state of a cartridge used in the assay apparatus.

FIG. 5 is a plan view illustrating the cartridge 20, removing the upper surface of the cartridge 20. The cartridge 20 will be described with reference to FIG. 5. The cartridge 20 includes an insoluble carrier 21, a cartridge case 22 for housing the insoluble carrier 21, a solution injection hole 23, and an observation window 24. The insoluble carrier 21 includes test line A, test line B, and control line C. The solution injection hole 23 is formed on the upper surface of the case to inject specimen solution onto the soluble carrier 21. The observation window 24 is provided to observe assay sites (test lines A, B and control line C portions) of the insoluble carrier 21. An information display unit 25 is provided on the upper surface of the cartridge case 22. Further, an observation window 14a that substantially matches with the observation window 24 is provided on the cartridge loading unit 14.

The insoluble carrier 21 includes an immobilized labeling substance. Further, each of the test lines A and B is formed by immobilizing a substance that specifically binds to an analyte. The control line C is provided to judge completion of measurement.

Further, an insoluble carrier 72 for supplying liquid and an insoluble carrier 73 for absorption are arranged on both sides of the insoluble carrier 21 in the cartridge 20. Further, the aforementioned washing liquid pot 27 is fixed at a position above the insoluble carrier 72 for supplying liquid, and the sensitizing solution pot 28 is fixed at a position above a control line C side end of the insoluble carrier 21.

Figure 8:
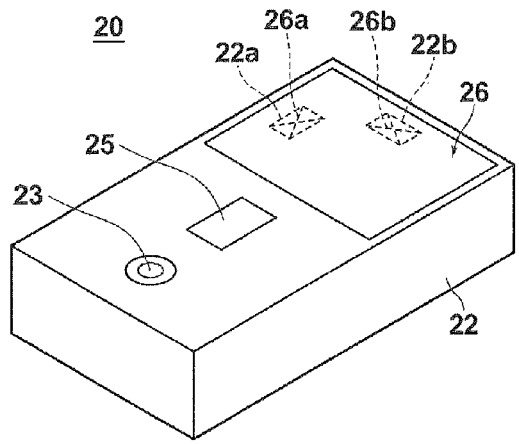
FIG. 8 is a perspective view illustrating the external shape of the cartridge.

FIG. 8 illustrates the shape of the cartridge 20 in detail. As illustrated in FIG. 8, openings 22a and 22b are formed in the upper surface of the case 22 just above the washing liquid pot 27 and the sensitizing solution pot 28, respectively. Further, the openings 22a and 22b are covered by a sheet material 26 made of paper, a thin synthetic resin sheet, or the like. The sheet material 26 is easily breakable when it is pushed from the upper side by the aforementioned pressure portions 32, 36, respectively. The sheet material 26 allows the pressure portion 32 to move through the opening 22a, and to squeeze the washing liquid pot 27. The sheet material 26 allows the pressure portion 36 to move through the opening 22b, and to squeeze the sensitizing solution pot 28.

In the present embodiment, perforation lines 26a are provided in the sheet material 26 along each of diagonal lines of the square openings 22a, 22b. Therefore, when the sheet material 26 is pressed from the upper side by the pressure portions 32, 36, the sheet material 26 is easily breakable along the perforation lines 26a.

Further, cutting tools may be arranged at positions above the washing liquid pot 27 and the sensitizing solution pot 28, respectively, and the washing liquid pot 27 and the sensitizing solution pot 28 may be cut open by the cutting tools pressured by the pressure portions 32, 36 that have moved down.

The first measurement unit 40 measures the color-developed state at assay sites (test lines A, B and control line C portions) through the observation window 24 of the cartridge 20. As illustrated in FIG. 2, the first measurement unit 40 includes a camera 42 and a light source 44. The first measurement unit 40 is structured in such a manner that the camera 42 and the light source 44 face the observation window 24 from the lower side of the cartridge 20 when the cartridge 20 is loaded into the assay apparatus 1. Further, optical density and chromaticity are calculated, as the color-developed state of the assay sites, based on the optical information about the assay sites obtained by the first measurement unit 40 (this will be described later).

Here, when the intensity of incident light entering an assay site in the cartridge 20 is I, and the intensity of reflection light from the assay site is $I_r$, the optical density is defined by the following formula:

$$\text{Optical Density} = -\log_{10}(I_r/I).$$

Further, chromaticity numerically represents hue and saturation. The chromaticity is calculated based on an RGB luminance signal read by the camera. A general CIE color system may be used as the color system of chromaticity.

The camera 42 includes an image sensor, for example, in which plural photodiodes are linearly arranged, or an area sensor. The camera 42 outputs a signal based on the light amount of received light. The light receiving range of the camera 42 is a band-shaped range extending along the longitudinal direction of the cartridge 20. The light source 44 is, for example, a module in which an LED is incorporated, and structured so as to output white light. The light source 44 may output, for example, light of a single color as long as a change in chromaticity by sensitizing process, which will be described later, is distinguishable. When the light source 44 is composed of plural modules, it may be composed of plural modules, each outputting light of a single color the wavelength of which is different from each other. Light output from the light source 44 can illuminate a predetermined range in the longitudinal direction of the cartridge 20.

Meanwhile, the second measurement unit 50 obtains information displayed on the information display unit 25 of the cartridge 20 by illuminating the information display unit 25 with illumination light. The information display unit 25 displays information about an assay by hand writing, by adhesion of a sticker, or the like. The information about an assay is, for example, information about a patient from whom an analyte has been collected (name, age, sex, and the like), information about a sample and a reagent used in the assay (an analyte that is a target of assay, the names of washing liquid, sensitizing solution, and the like), and the like. The method for obtaining the information is not particularly limited. What is displayed on the information display unit 25 may be directly imaged, or bar-coded information may be read.

As illustrated in FIG. 2, the second measurement unit 50 includes a camera 52 and a light source 54. The second measurement unit 50 is structured in such a manner that the camera 52 and the light source 54 face the information display unit 25 from the upper side of the cartridge 20 when the cartridge 20 is loaded into the assay apparatus 1. Further, the information about the assay obtained by the second measurement unit 50 and an assay result are managed in such a manner that they are linked with each other. Specific structures of the camera 52 and the light source 54 are similar to those of the camera 42 and the light source 44, which have already been described, respectively.

Next, the electrical configuration of the apparatus of the present invention will be described with reference to FIG. 3. Operations of the display unit 11, the operation unit 12, the pressure mechanisms 30, 34 including the motor 38 and the like, and the cameras 42, 52 (including the light sources 44, 54, respectively), which have already been described, are controlled by a control unit 80 illustrated in FIG. 3. Further, the assay apparatus 1 of the present invention can operate, for example, by using a commercial electric power source of 100 through 240V. The assay apparatus 1 includes an electric power source unit 100 for converting electricity received from the commercial electric power source into direct current of 12V, and a switch unit 101 to which the direct current of 12V is input. Further, the assay apparatus 1 of the present invention can be driven by a battery 102, which is a secondary battery. The battery 102 is also connected to the switch unit 101. The switch unit 101 performs switching in such a manner that direct current of 12V supplied from the electric power source unit 100 is used by each electrical part when the switch unit 101 is connected to the commercial electric power source, and that direct current of 12V supplied from the battery 102 is used by each electrical part when the switch unit 101 is not connected to the commercial electric power source.

Further, a battery capacity monitor unit 103 is connected to the switch unit 101. The battery capacity monitor unit 103 is a battery remaining-amount detection means for detecting the remaining electric power amount of the battery 102. Generally, because of the chemical properties of a battery, the internal resistance of the battery increases as the capacity of the battery becomes lower, and terminal voltage of the battery becomes lower. Therefore, it is possible to detect the remaining electric power amount of the battery by measuring the terminal voltage of the battery. The battery capacity monitor unit 103 continues detection of the remaining electric power amount of the battery 102 in this manner, and inputs a signal representing the remaining electric power amount to the control unit 80.

Next, the action of the assay apparatus 1 in the present embodiment will be described. In principle, the apparatus of the present invention performs first stage measurement for testing a specimen solution and second stage measurement, which follows the first stage measurement. The first stage measurement measures the color-developed state of the assay sites without sensitizing process, which will be described later. The second stage measurement measures the color-developed state of the assay sites after sensitizing process, which will be described later.

Next, specific measurement operation steps will be described. The flow of these steps is illustrated in the flow chart of FIG. 11.

<<First Stage Measurement>>

In the first stage measurement, first, specimen solution 90 is injected through the solution injection hole 23 of the cartridge 20 located on the outside of the assay apparatus 1, for example, as illustrated in FIG. 5. Then, the cartridge 20 is inserted in the assay apparatus 1, as already described (Step S1 in FIG. 11, and so on). Next, the control unit 80 illustrated in FIG. 3 judges whether measurement has been aborted by detecting whether the cartridge loading unit 14 has been extracted for some reasons other than predetermined routines, or the like (step S2).

Here, when it has been judged that measurement has not been aborted, the camera 42 obtains images of assay sites (test lines A, B and control line C portions) in the cartridge 20 to calculate the optical density and the chromaticity of each of the assay sites. The control unit 80 calculates the optical densities and the chromaticities based on the images obtained in this manner, and displays the calculated values, or an assay result, such as the presence or non-presence of a disease, which has been judged based on the values on the display unit 11 (step S3).

<<Second Stage Measurement>>

Figure 6:
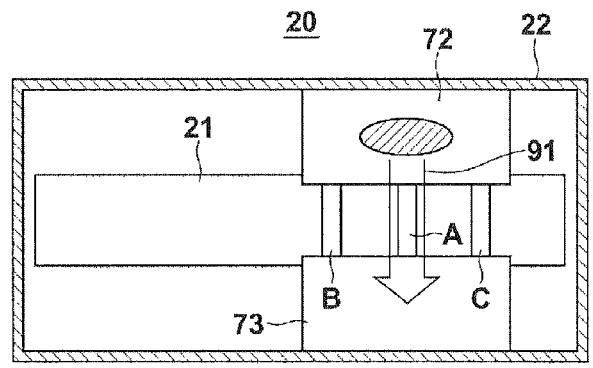
FIG. 6 is a partially-broken plan view illustrating another state of the cartridge.

Next, the control unit 80 judges whether an amplification (sensitizing) process is necessary based on the aforementioned judgment result (step S4). When the control unit 80 has judged that an amplification process is necessary, the second stage measurement is performed. In the second stage measurement, first, the pressure unit 30 illustrated in FIGS. 2 and 4 is driven, and the leading end of the arm 31 of the pressure unit 30 moves down, and a hole is made at the opening 22*a* portion of the sheet material 26 (step S5). Further, the pressure portion 32 that has passed through the opening 22*a* squeezes the washing liquid pot 27 in the cartridge 20 from the outside of the cartridge 20. Accordingly, as illustrated in FIG. 6, washing liquid 91 stored in the washing liquid pot 27 washes the assay site of the insoluble carrier 21. At this time, the washing liquid 91 is supplied to the insoluble carrier 21 and the insoluble carrier 73 for absorption in this order after the washing liquid 91 has sufficiently spread on the insoluble carrier 72 for supplying liquid.

Figure 7:
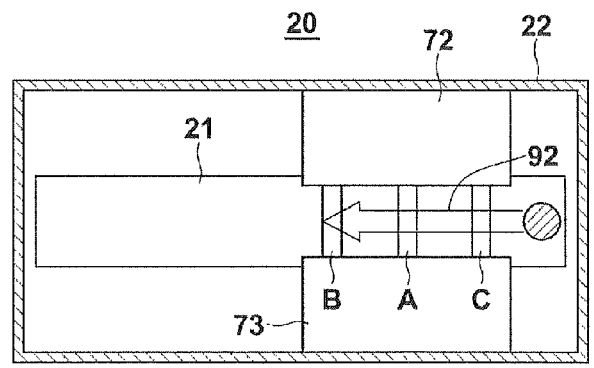
FIG. 7 is a partially-broken plan view illustrating still another state of the cartridge.

Next, the pressure unit 34 illustrated in FIGS. 2, 4 is driven, and the leading end of the arm 35 of the pressure unit 34 moves down, and a hole is made at the opening 22*b* portion of the sheet material 26 (step S5). Further, the pressure portion 36 that has passed through the opening 22*b* squeezes the sensitizing solution pot 28 in the cartridge 20 from the outside of the cartridge 20. Accordingly, as illustrated in FIG. 7, sensitizing solution 92 stored in the sensitizing solution pot 28 is supplied to the assay site of the insoluble carrier 21, and sensitization is performed (step S6). The sensitizing solution 92 and the washing liquid 91 are disclosed in detail in Patent Document 3, and the disclosure of Patent Document 3 is adoptable also in the present invention.

After the sensitizing process, images of the assay sites in the cartridge 20 are imaged by the camera 42 in a manner similar to the aforementioned case. The control unit 80 calculates the optical densities and the chromaticities of the images obtained in this manner, and displays the calculated values, or an assay result, such as the presence or non-presence of a disease, judged based on the values on the display unit 11 (step S7). After then, the cartridge 20 is extracted from the assay apparatus 1 (step S8).

Next, matters related to the measurement will be briefly described.

(Specimen Solution)

Specimen solution that can be assayed by using the assay apparatus of the present invention is not particularly limited as long as the specimen solution may contain an analyte (a physiologically active substance, such as natural products, a toxin, a hormone or an agricultural chemical, an environmental pollutant, and the like). Examples of the specimen solution are a biological sample, in particular, body fluids (for example, blood, blood serum, blood plasma, spinal fluid, lacrimal fluid, sweat, urine, pus, nasal mucus or sputum) or excrements (for example, feces), organs, tissues, mucosae and skin of an animal (particularly, a human), a swab specimen (swab), and a gargle specimen that may contain such a substance, animals or plants themselves or dried bodies thereof diluted with a diluting agent that will be described later, and the like.

The specimen solution may be used directly, or in the form of extracted solution obtainable by using a solvent for extraction appropriate for the specimen solution, or in the form of diluted solution obtainable by further diluting the extracted solution with an appropriate diluting agent, or in the form of condensed solution obtainable by condensing the extracted solution using an appropriate method.

(Labeling Substance)

A labeling substance usable in the present invention is not particularly limited as long as the labeling substance has a color and is visually recognizable, or the labeling substance becomes testable by reaction. For example, the labeling substance may be metal particles (or metal colloid), colored latex particles, enzymes, or the like, which are used in general immunochromatography. When signals are amplified by deposition of metal on a labeling substance by a reduction reaction of metal ions with the labeling substance acting as a catalyst, it is desirable to use metal particles from the view point of the catalytic activity thereof.

As the material of the metal particles, a simple metal, a metal sulfide, a metal alloy, or a polymer particle label containing metal may be used. It is desirable that the average particle diameter of the particles (or colloid) is in the range of 1 nm to 10 μm. Here, the average particle diameter is an average value of diameters (the largest diameter of each particle) of plural particles actually measured by a transmission electron microscope (TEM). Specifically, gold colloid, silver colloid, platinum colloid, iron colloid, aluminum hydroxide colloid, composite colloid thereof, and the like may be used. It is desirable to use gold colloid, silver colloid, platinum colloid, and composite colloid thereof. Especially, gold colloid, silver colloid and composite colloid thereof are desirable. They are desirable because the gold colloid shows red, and the silver colloid shows yellow when the particle diameters are appropriate, and they are easily visually recognizable. When the gold colloid is used, the chromaticity of the label changes after a sensitizing process using a silver ion containing compound (the gold colloid shows red, and after the sensitizing process, the red color changes to black by deposition of reduced silver ions on the gold colloid). This change can be used to judge an error in assay, as will be described later. As the average particle diameter of metal colloid, about 1 to 500 nm is desirable, and 1 to 100 nm is more desirable.

(Specific Binding Substance)

The specific binding substance is not particularly limited as long as it has an affinity for an analyte. For example, when the analyte is an antigen, an antibody to the antigen may be used. When the analyte is protein, metal ions, or low molecular weight organic compound, aptamers to them may be used. When the analyte is a nucleic acid, such as DNA and RNA, nucleic acid molecules, such as DNA and RNA, that have complementary sequence to the nucleic acid may be used. When the analyte is avidin, biotin may be used. When the analyte is a specific peptide, a complex specifically binding to the peptide, or the like may be used. In the aforementioned examples, the specific binding substance and the analyte that are related to each other may be switchable therebetween. For example, when the analyte is an antibody, an antigen to the antibody may be used as a specific binding substance. Further, a compound a part of which contains a substance having an affinity for the analyte, as described above, or the like may be used as a specific binding substance.

Specifically, as the antibody, an antiserum prepared from an animal serum immunized with the analyte, an immunoglobulin fraction purified from the antiserum, a monoclonal antibody obtained by cell fusion using animal splenocytes immunized with the analyte, or fragments thereof [for example, F(ab')2, Fab, Fab', or Fv] may be used. Preparation of these antibodies may be performed by using common methods.

(Insoluble Carrier)

It is desirable that the material of the insoluble carrier 21 is porous. For example, a nitrocellulose membrane, a cellulose membrane, an acetyl cellulose membrane, a polysulfone membrane, a polyether sulfone membrane, a nylon membrane, glass fibers, a nonwoven fabric, a fabric, a thread, and the like are desirable.

An assay line is formed on a chromatographic carrier by immobilizing a specific binding substance to an analyte onto a chromatographic carrier. Further, a control site is prepared, if desirable. The specific binding substance may be directly immobilized on a part of the chromatographic carrier by physical or chemical bond. Alternatively, the specific binding substance may be bound to a particle, such as a latex particle, and the particle may be trapped on a part of the chromatographic carrier to immobilize the specific binding substance.

(Sensitizing Solution)

The sensitizing solution can amplify signals by forming a compound that shows color or produces luminescence or the like by reaction of a chemical contained in the solution by a catalystic action of a labeling substance or an analyte. For example, the sensitizing solution is a silver ion solution that makes metal silver precipitate on the metal label by physical development. Particularly, a so-called developer as described in general books in the field of photographic chemistry (for example, "Revised Basic Photographic Engineering—Silver Salt Photography" (The Society of Photography and Imaging of Japan, CORONA PUBLISHING CO., LTD.), "Chemistry of Photography" (Akira Sasai, Photography Industry Publishing Co., Ltd.), "Newest Formulation Handbook" (Shinichi Kikuchi, et al., AMIKO Publishing Co., Ltd.) may be used. For example, when a physical developer containing a silver ion containing compound is used as the sensitizing solution, a reducing agent of silver ions can reduce silver ions in the solution to make silver deposit on metal colloid or the like that forms a core for development, as a center.

As another example, an enzyme reaction may be used. For example, a solution of a phenylenediamine compound and a naphthol compound, which forms a dye through an action between a peroxidase label and hydrogen peroxide, may be used. Alternatively, a color-developing substrate for detecting horseradish peroxidase, as disclosed in Non-Patent Document "Dyeing Using $H_2O_2$-POD System, Clinical Test, Vol. 41, No. 9, pp. 1020-1024", or the like may be used. Further, a color-developing substrate disclosed in Japanese Unexamined Patent Publication No. 2009-156612 is especially preferable. Further, a system using a metal catalyst, such as platinum particles, instead of an enzyme may be used.

Another example using an enzyme is a system that develops color by using alkaline phosphatase as a label, and 5-bromo-4-chloro-3-indolyl-phosphate disodium salt (BCIP) as a substrate. So far, color development reactions have been described as representative examples. However, any combination of an enzyme and a substrate generally used in enzyme immunoassay may be used. The substrate may be a chemiluminescent substrate or a fluorescent substrate.

(Silver Ion Containing Compound)

As a silver ion containing compound, an organic silver salt, an inorganic silver salt, or a silver complex may be used. It is desirable that the silver ion containing compound is highly soluble in a solvent, such as water, and examples of the silver ion containing compound is silver nitrate, silver acetate, silver lactate, silver butyrate and silver thiosulfate. Especially, silver nitrate is desirable. It is desirable that the silver complex has a ligand having water-soluble group, such as hydroxyl group or sulfonic group, and an example of the silver complex is hydroxythioether silver, or the like. The inorganic silver salt or the silver complex may contain 0.001 mol/m² to 0.2 mol/m² of silver. Further, it is more desirable that the inorganic silver salt or the silver complex contains 0.01 mol/m² to 0.05 mol/m² of silver.

(Silver Ion Reducing Agent)

A silver ion reducing agent may be any inorganic or organic material or a mixture thereof as long as the agent can reduce silver ions into silver.

As the inorganic reducing agent, reducing metal salts and reducing metal complex salts having a metal ion with a variable valence, such as $Fe^{2+}$, $V^{2+}$ or $Ti^{3+}$, are preferable. When an inorganic reducing agent is used, it is necessary to complex or reduce the oxidized ion to remove the oxidized ion or to make the oxidized ion harmless. For example, in a system using $Fe^{2+}$ as the reducing agent, a complex of $Fe^{3+}$ that is an oxide may be formed by using citric acid or EDTA to make the oxidized ion harmless. In the system of the present invention, it is desirable to use such an inorganic reducing agent, and it is more desirable to use a metal salt of $Fe^{2+}$.

In the aforementioned embodiment, as a method for amplifying the color-developed state, a method for sensitizing a labeling substance by reducing a silver ion containing compound with a reducing agent was used. However, the sensitizing method in the present invention is not limited to such a method. The sensitizing solution may be any solution as long as the solution can amplify a signal by forming a compound that shows color or produces luminescence by reaction of a chemical contained in the solution by a catalytic action of the labeling substance or the analyte. For example, a solution using an enzyme, as described above, may be used.

In the aforementioned embodiments, immunochromatography was described as the assay method. However, the assay method adopted in the present invention is not limited to immunochromatography. It is not necessary that the system uses a so-called immune reaction. For example, the system may capture an analyte using a nucleic acid, such as DNA or RNA, without using an antibody. Further, the system may capture an analyte using a different small molecule, a peptide, a protein, a complex forming substance, or the like, which has an affinity for the analyte.

Figure 9:
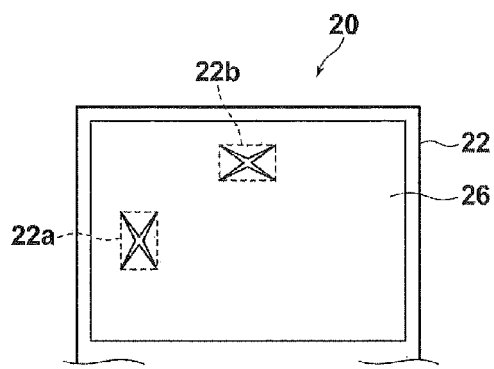
FIG. 9 is a partial plan view illustrating a state of the cartridge after use.

When the first stage measurement and the second measurement as described above have been performed, the sheet material 26 of the cartridge 20 becomes, as illustrated in FIG. 9. Specifically, the portions of the sheet material 26 matched with the openings 22a, 22b are broken by the aforementioned pressure portions 32, 36, respectively, and holes are made. Therefore, when the cartridge 20 is extracted from the chromatographic assay apparatus 1 after the assay is completed, it is possible to recognize, based on the presence of the holes, that the cartridge 20 has been used. Hence, it is possible to prevent erroneous reuse of the used cartridge 20.

However, when the measurement has been aborted, as described above, or when only the first stage measurement has been performed, the cartridge 20 extracted directly from the chromatographic assay apparatus 1 does not have the holes. Therefore, there is a risk of erroneously using the cartridge 20 again. Next, features for preventing this problem will be described.

Figure 11:
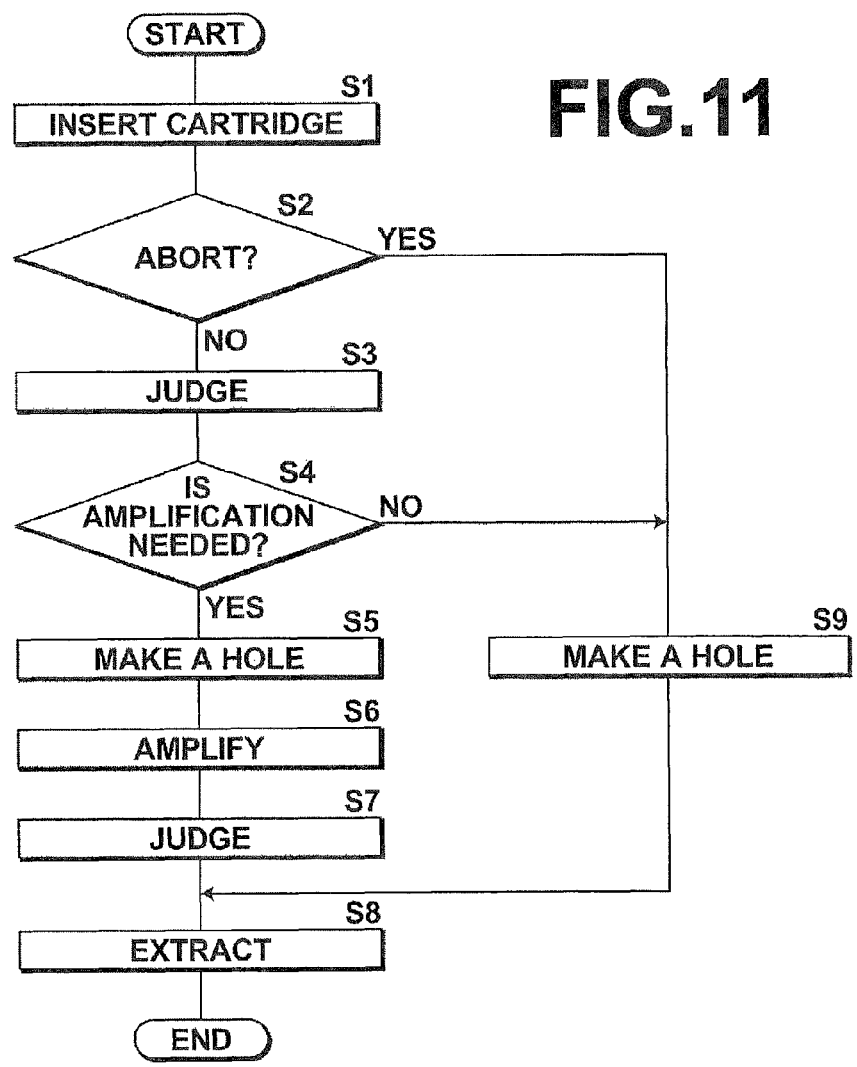
FIG. 11 is a flow chart illustrating steps during assay by the assay apparatus.

When the control unit 80 illustrated in FIG. 3 has judged that the assay ended before completion, in other words, when the control unit 80 has judged that the measurement was aborted in step S2 illustrated in FIG. 11, or when it was judged in step S4 that an amplification process was not necessary, the control unit 80 drives the pressure units 30, 34 to make holes in the sheet material 26 at portions matching with the openings 22a, 22b by the pressure portions 32, 36, respectively (step S9). Accordingly, it is possible to recognize that the cartridge 20 extracted from the chromatographic assay apparatus 1 has been used also in this case, because the holes are formed. Hence, it is possible to prevent erroneous reuse of the cartridge 20.

As clearly described, in the present embodiment, the control unit 80 constitutes a means for detecting a state in which an assay has ended before completion. Further, the pressure portions 32, 36 and a mechanism for driving the pressure portions 32, 36 constitute a means for providing a predetermined mark for the cartridge 20, as a reaction container.

As described above, when holes are made in the sheet material 26 at openings 22a, 22b that are located at positions matching with the washing liquid pot 27 and the sensitizing solution pot 28, respectively, it is desirable that each of the openings of the washing liquid pot 27 and the sensitizing solution pot 28 is covered by an independent sheet material for sealing liquid, and that the sheet material 26 is placed above the independent sheet materials with some space therefrom. If such a double sheet structure is adopted, when the aforementioned sensitizing process is performed, both of the sheet material 26 and the sheet materials for sealing liquid may be broken by the pressure portions 32, 36 by setting relatively large downward strokes of the arms 31, 35. In contrast, when a hole, as a mark indicating that the cartridge 20 has been used, is made in the sheet material 26, only the sheet material 26 may be broken by the pressure portions 32, 36 by setting relatively small downward strokes of the arms 31, 35. In this manner, it is possible to prevent unnecessary flow of the washing liquid and the sensitizing solution when a hole, as a mark indicating that the cartridge 20 has been used, is made in the sheet material 26.

Figure 10:
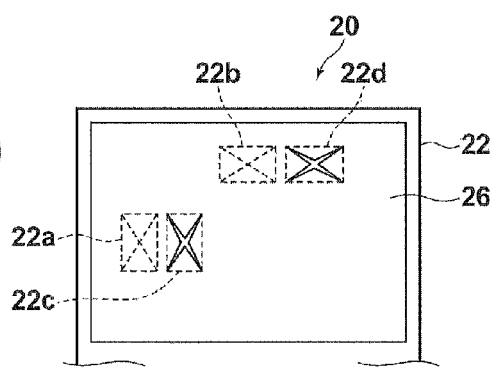
FIG. 10 is a partial plan view illustrating a state of the cartridge after use in another embodiment of the present invention.

Further, as illustrated in FIG. 10, additional openings 22c, 22d may be provided in the vicinity of the openings 22a, 22b, and holes may be made at the openings 22c, 22d in the sheet material 26. In this case, even if the aforementioned double sheet structure is not adopted, and the washing liquid pot 27 and the sensitizing solution pot 28 are covered only by the sheet material 26, it is possible to prevent unnecessary flow of the washing liquid and the sensitizing solution when a hole, as a mark indicating that the cartridge 20 has been used, is made in the sheet material 26.

When the additional openings 22c, 22d are provided, a specialized mechanism for making holes at the openings 22c, 22d in the sheet material 26 may be provided. Alternatively, the pressure units 30, 34 may make holes in the sheet material 26 in a manner similar to the aforementioned case. In the latter case, a means for relatively moving the pressure units 30, 34 and the cartridge loading unit 14 in the direction in which the opening 22a and the opening 22c (the opening 22b and the opening 22d) are arranged may be provided. The relative movement should make the pressure portions 32, 36 match with the openings 22a, 22b when a sensitizing process is performed, and the relative movement should make the pressure portions 32, 36 match with the openings 22c, 22d when a hole, as a mark indicating that the cartridge 20 has been used, is made in the sheet material 26.

Instead of providing the openings 22a, 22b as described above, and covering the openings 22a, 22b with the sheet material 26, a portion of the cartridge case wall corresponding to the position at which each of the openings 22a, 22b is set may be thinly formed to lower the strength of the portion. Then, the portions may be broken by the pressure portions 32, 36 to make holes.

Further, instead of making holes in the cartridge case 22 as described above, a mark indicating that the cartridge 20 has been used may be drawn on the surface of the cartridge case 22 using oil-based ink, or the like.

What is claimed is:

1. An assay apparatus for performing an assay related to a specimen received from the outside thereof based on a reaction between the specimen and a reagent by using a reaction container that holds the reagent, the apparatus comprising:
   detection means for detecting a state in which an assay has ended irregularly before completion; and
   mark providing means for providing a predetermined mark for the reaction container when the state in which the assay has ended irregularly before completion is detected by the detection means;
   wherein the mark providing means makes a hole, as the mark, in a surface of the reaction container.

2. An assay apparatus, as defined in claim 1, wherein means that is used to break a protective sheet protecting the reagent is used also as the mark providing means.

3. A reaction container for an assay that is used in the assay apparatus, as defined in claim 1, wherein an opening is provided on the surface of the reaction container, and the opening is covered by a sheet material that is breakable by the mark providing means.

4. A reaction container for an assay, as defined in claim 3, wherein a double sheet structure is formed by providing, under the sheet material that is breakable, another sheet material for sealing the reagent with a space from the sheet material that is breakable.

5. A reaction container for an assay that is used in the assay apparatus, as defined in claim 1, wherein a part of the surface of the reaction container has a low strength so that the hole is made by the mark providing means.

6. A method for controlling an assay apparatus that performs an assay related to a specimen received from the outside thereof based on a reaction between the specimen and a reagent by using a reaction container for an assay that holds the reagent, as defined in claim 5, the method comprising:
   detecting a state in which an assay has ended irregularly before completion; and
   making a hole, as a predetermined mark, in the surface of the reaction container when the state in which the assay has ended irregularly before completion is detected by the detection means,
   wherein when the assay is performed, both of a breakable sheet material and an other sheet material are broken to allow the reagent to flow out, and
   wherein when the hole, as the mark, is made, only the breakable sheet material is broken.

7. A reaction container for an assay that is used in the assay apparatus, as defined in claim 3, wherein the sheet material includes perforation lines along diagonal lines of the opening.

8. A reaction container for an assay that is used in the assay apparatus, as defined in claim 1, wherein a second opening is provided in the surface of the reaction container corresponding to a position different than a position of the reagent, and the second opening is covered by a sheet material that is breakable by the mark providing means.

9. A reaction container for an assay that is used in the assay apparatus, as defined in claim 3, wherein a second opening is provided on the surface of the reaction container at a position different than a position of the opening, and the second opening is covered by the sheet material that is breakable by the mark providing means.

10. A reaction container for an assay that is used in the assay apparatus, as defined in claim 9, further comprising means for relatively moving the predetermined mark such that the mark providing means makes the hole, as the mark, in the surface of the reaction container corresponding to the second opening.

* * * * *